United States Patent
El A'mma

(10) Patent No.: US 6,211,213 B1
(45) Date of Patent: Apr. 3, 2001

(54) STABLE MICROBICIDE FORMULATION

(75) Inventor: Beverly Jean El A'mma, Perkiomenville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/547,407

(22) Filed: Apr. 12, 2000

Related U.S. Application Data

(60) Provisional application No. 60/129,813, filed on Apr. 16, 1999.

(51) Int. Cl.[7] .......................... A01N 43/80; A01N 31/00; A01N 31/02; A01N 37/00; A01N 59/20
(52) U.S. Cl. .......................... 514/372; 514/373; 514/557; 514/558; 514/559; 514/560; 514/568; 514/570; 514/574; 514/714; 514/970; 514/971; 514/973; 424/613; 424/615; 424/616; 424/630; 424/631; 424/632; 424/633; 424/634; 424/635; 424/637; 424/638; 504/151; 504/152; 504/156
(58) Field of Search .................................... 514/372–373, 514/557–560, 568, 570, 574, 714, 970, 971, 973; 424/613, 615–616, 630–635, 637–638; 504/151, 152, 156

(56) References Cited

U.S. PATENT DOCUMENTS

| 5,153,213 | 10/1992 | Schmidt | 514/372 |
| 5,461,150 | 10/1995 | Gironda et al. | 548/213 |
| 5,599,827 | 2/1997 | Gironda | 514/372 |

FOREIGN PATENT DOCUMENTS

| 147223 A2 | 7/1985 | (EP) . |
| 0606986 | 7/1994 | (EP) . |
| 0721736 | 7/1996 | (EP) . |
| 0749689 | 12/1996 | (EP) . |
| 773281 * | 5/1997 | (EP) . |
| 0875145 | 11/1998 | (EP) . |

OTHER PUBLICATIONS

European Search Report, Application # EP 00 30 2826, Aug. 17, 2000.
Annex to the European Search Report on European Patent Application #EP 00 30 2826, Aug. 17, 2000.

* cited by examiner

*Primary Examiner*—John Pak
(74) *Attorney, Agent, or Firm*—Joanne P. Will; S. Matthew Cairns; Thomas J. Howell

(57) ABSTRACT

Stable microbicidal compositions containing a 3-isothiazolone compound, organic oxidants, copper salts and water are disclosed. Also disclosed are methods of stabilizing 3-isothiazolone compositions.

10 Claims, No Drawings

STABLE MICROBICIDE FORMULATION

This application claims th benefit of U.S. Provisional Application Ser. No. 60/129,813, filed on Apr. 16, 1999.

BACKGROUND OF THE INVENTION

This invention relates to the stabilization of microbicides. In particular, this invention relates to the improved stabilization of 3-isothiazolone dilute solution compositions.

Microbicides are used commercially to prevent the growth of microbes in a variety of loci, such as cooling towers, metal working fluid systems, paint and cosmetics. One of the more important classes of microbicides is 3-isothiazolones. Many 3-isothiazolones have achieved commercial success because they are very effective in preventing microbial growth under a wide variety of conditions and in a variety of loci. Among the most important 3-isothiazolones are 5-chloro-2-methyl-3-isothiazolone, 2-methyl-3-isothiazolone, and mixtures thereof.

While 3-isothiazolones are very effective microbicides, they suffer from being unstable under certain conditions. Without the presence of a stabilizer, many 3-isothiazolones chemically degrade and lose microbicidal efficacy. Much research has been devoted to stabilizing 3-isothiazolones.

In general, compounds that stabilize 3-isothiazolone concentrates do not stabilize 3-isothiazolone dilute solutions. Compounds, such as magnesium nitrate, that do stabilize both 3-isothiazolone concentrates and dilute solutions do so in greatly differing amounts. More magnesium nitrate is required to stabilize a 3-isothiazolone dilute solution than a concentrate; 23 percent by weight for dilute solutions as compared to 12 to 16 percent by weight for concentrates. As dilute solutions are typically prepared by diluting 3-isothiazolone concentrate compositions, this need for additional stabilizer results in increased cost and handling.

Typical 3-isothiazolone products of a 3:1 mixture of 5-chloro-2-methyl-3-isothiazolone and 2-methyl-3-isothiazolone contain between 1 and 25 percent by weight of the 3-isothiazolone mixture and a similar amount of a stabilizer. Concentrate compositions of a 3:1 mixture of 5-chloro-2-methyl-3-isothiazolone and 2-methyl-3-isothiazolone generally contain about 5 to 35 percent by weight of the 3-isothiazolone compounds and require about 10 to 25 percent by weight of a stabilizer, such as magnesium nitrate. Dilute solutions of a 3:1 mixture of 5-chloro-2-methyl-3-isothiazolone and 2-methyl-3-isothiazolone contain about 0.5 to 5 percent by weight of the 3-isothiazolone compounds.

Dilute solutions of 3-isothiazolones are usually stabilized either with high levels of magnesium nitrate (23 wt %), with a combination of magnesium nitrate (1.5–5 wt %) and very low levels of copper nitrate (0.037–0.14 wt % as copper ion), with a combination of magnesium nitrate (4–5 wt %) and copper sulfate (4 wt %), or with a low levels of hydrogen peroxide.

These known stabilized 3-isothiazolone dilute solutions suffer from having a high metal salt content or having limited stability. When a 3-isothiazolone stabilized with a metal salt is added to a latex formulation, the high metal salt content can coagulate the latex. Although the above described stabilizers for 3-isothiazolone dilute solutions allow the 3-isothiazolones to retain their microbicidal efficacy for considerable periods of time, they do not prevent other problems from developing, such as the formation of precipitate upon storage.

The presence of this precipitate does not impact the efficacy of the 3-isothiazolones; however, the presence of the precipitate gives an undesirable appearance to users of the product. It is clearly preferable from a commercial standpoint to have a product which does not form a precipitate.

U.S. Pat. No. 5,461,150 (Gironda, et al.), herein incorporated by reference, discloses the stabilization of 3-isothiazolone concentrates with a low level of cupric ion. While these compositions are stable, they suffer from the formation of a brown precipitate upon storage. Such brown precipitate is particularly undesirable when such compositions are used to preserve cosmetics and toiletries. Gironda et al. do not address the problem of precipitate formation upon storage of the 3-isothiazolone compositions.

Thus, there is a continuing need for stable 3-isothiazolone dilute solution compositions that remain stable and do not form precipitate upon storage.

SUMMARY OF THE INVENTION

It has now been found that 3-isothiazolone dilute solution compositions can be effectively stabilized by organic oxidants in the presence of a small amount of cupric ion in the form of a copper salt while avoiding the problems of coagulation of latexes, limited stability of the 3-isothiazolones, and precipitate formation upon storage.

The present invention is directed to a stable microbicide composition comprising: (a) 0.1 to 5 wt %, based on the weight of the composition, of a water soluble 3-isothiazolone; (b) 0.0001 to 0.3 wt %, based on the weight of the composition, of one or more organic oxidants; (c) 0.0001 to 0.02 wt %, based on the weight of the composition, of a cupric ion in the form of a copper salt; and (d) water; wherein the composition is free of brown precipitate for at least 12 weeks at 40° C.

The present invention is also directed to a method of stabilizing a microbicide composition comprising the step of adding 0.0001 to 0.3 wt %, based on the weight of the composition, of one or more organic oxidants; and 0.0001 to 0.02 wt %, based on the weight of the composition, of a cupric ion in the form of a copper salt to a 3-isothiazolone composition comprising 0.1 to 5 wt %, based on the weight of the composition, of a water soluble 3-isothiazolone compound; and water.

The present invention is also directed to a method of controlling or inhibiting the growth of microorganisms in a locus comprising introducing to the locus a composition as described above.

DETAILED DESCRIPTION OF THE INVENTION

As used throughout the specification, the following terms shall have the following meanings, unless the context clearly indicates otherwise.

The term "microbicide" refers to a compound capable of inhibiting the growth of or controlling the growth of microorganisms at a locus. The term "microorganism" includes, but is not limited to, fungi, bacteria, and algae. The term "locus" refers to an industrial system or product subject to contamination by microorganisms.

The following abbreviations are used throughout the specification: HPLC=high performance liquid chromatography; C=centigrade; ppm=parts per million; g=gram; DI=deionized; and wt %=percent by weight.

Unless otherwise noted, all amounts are percent by weight and all ratios are by weight. All numerical ranges are inclusive.

Any water soluble 3-isothiazolone compound is useful in the compositions of the present invention. Water soluble 3-isothiazolone compounds are those having a water solubility greater than 1000 ppm. Suitable 3-isothiazolone compounds include, but are not limited to: 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; and mixtures thereof. Preferred 3-isothiazolones are 5-chloro-2-methyl-3-isothiazolone and 2-methyl- 3-isothiazolone, either alone or in admixture. When mixtures of 5-chloro-2-methyl-3-isothiazolone and 2-methyl-3-isothiazolone are used, the weight ratio of 5-chloro-2-methyl-3-isothiazolone to 2-methyl-3-isothiazolone is generally 99:1 to 1:99, preferably 10:1 to 3:1.

The amount of water soluble 3-isothiazolone compound useful in the compositions of the present invention is 0.1 to 5 wt %, based on the weight of the composition. It is preferred that the amount of 3-isothiazolone compound is 0.2 to 4 wt %; and more preferably, 0.5 to 2 wt %.

A wide variety of organic oxidants are known in the art. Any organic oxidant which is sufficiently water soluble to provide an effective level of oxidant in solution may be used in the compositions of the present invention. Organic oxidants that are slightly water soluble, such as methyl ethyl ketone peroxide and tert-butyl peroxybenzoate, may be used advantageously in the present invention. The amount of slightly soluble organic oxidants in the compositions may be increased by using a solubilizer, such as a cosolvent or a surfactant. Suitable cosolvents include, but are not limited to: glycols, such as ethylene glycol, diethylene glycol, polyethylene glycol, propylene glycol, dipropylene glycol, polypropylene glycol; glycol ethers, such as polyethylene glycol methyl ether; esters, such as methyl acetate, ethyl acetate, and butyl acetate; and alcohols, such as methanol, ethanol, propanol, iso-propanol and butanol.

Suitable organic oxidants include, but are not limited to: peroxides, such as hydroperoxides, peroxydicarbonates, peroxyesters, peroxyketals, and diacyl peroxides; peracids; and persulfates. More than one organic oxidant may be used advantageously in the compositions of the present invention. Examples of suitable organic oxidants include, but are not limited to: tert-butyl hydroperoxide, 2,5-dihydroperoxy-2,5-dimethylhexane, di-tert-butyl hydroperoxide, 2-butanone peroxide, tert-butyl peroxybenzoate, tert-butyl peroxyacetate, tert-butyl peracetate, tert-butyl peroctoate, benzoyl-peroxide, succinic acid peroxide, urea peroxide, peracetic acid and mixtures thereof. It is preferred that the organic oxidants are tert-butyl hydroperoxide, 2,5-dihydroperoxy-2,5-dimethylhexane, di-tert-butyl hydroperoxide, and benzoyl-peroxide.

The amount of organic oxidant useful in the compositions of the present invention is 0.0001 to 0.3 wt %, based on the weight of the composition. It is preferred that the amount of organic oxidant is 0.0025 to 0.2 wt %, and more preferably 0.004 to 0.1 wt %. The organic oxidants are generally commercially available, for example, from Aldrich Chemical Company (Milwaukee, Wis.), and may be used without further purification.

A wide variety of copper salts are known in the art. Any copper salt which is sufficiently water soluble to provide the desired level of cupric ion in solution may be used in the compositions of the present invention. Suitable examples include, but are not limited to: copper sulfate, copper acetate, copper chloride, copper bromide, copper chlorate, copper perchlorate, copper nitrite and copper nitrate. Copper sulfate, copper chlorate, copper perchlorate and copper nitrate are preferred. Copper sulfate, copper chlorate and copper perchlorate are more preferred. The copper salts are generally commercially available, for example, from Pfalz and Bauer (Waterbury, Conn.), and may be used without further purification. Mixtures of copper salts may also be used.

The amount of copper ion useful in the compositions of the present invention is 0.0001 to 0.02 wt %, based on the weight of the composition, preferably 0.0005 to 0.015 wt %, and more preferably 0.001 to 0.01 wt %.

The weight ratio of organic oxidant to copper salt is typically 25:1 to 1:25. It is preferred that the weight ratio of organic oxidant to copper salt is in the range of 20:1 to 1:10, and more preferably 15:1 to 1:5. It is preferred that the organic oxidant be used in stoichiometric amounts to the copper ion.

Particularly useful compositions of the present invention include 0.5 to 1.5 wt % of a water soluble 3-isothiazolone selected from the group consisting of 5-chloro-2-methyl-3-isothiazolone; 2-methyl-3-isothiazolone; and mixtures thereof; 0.0025 to 0.2 wt % of an organic oxidant selected from tert-butyl hydro-peroxide, 2,5-dihydroperoxy-2,5-dimethylhexane, di-tert-butyl hydroperoxide, or benzoylperoxide; 0.0005 to 0.015 wt % cupric ion in the form of a copper salt selected from copper sulfate, copper chlorate or copper perchlorate; and water. All percentages used above are based on the weight of the composition.

In another embodiment, the compositions of the present invention may further comprise a water-miscible organic solvent. Any water miscible organic solvent that does not react with the 3-isothiazolone or organic oxidant is suitable. Examples of water miscible organic solvents include, but are not limited to: glycols, such as ethylene glycol, diethylene glycol, polyethylene glycol, propylene glycol, dipropylene glycol, polypropylene glycol; glycol ethers, such as polyethylene glycol methyl ether; esters, such as methyl acetate, ethyl acetate, and butyl acetate; and alcohols, such as methanol, ethanol, propanol, iso-propanol and butanol. Preferred organic solvents are those that aid in solubilizing the organic oxidant.

In preparing the compositions of the present invention, the organic oxidant cannot be added directly to the 3-isothiazolone alone. Otherwise, the 3-isothiazolone, organic oxidant, copper salt, and water can be mixed in any order. The compositions of the present invention are preferably prepared by adding the 3-isothiazolone to a mixture of organic oxidant, copper salt, and water.

An advantage of the compositions of the present invention is that they show no visible brown precipitate formation after storage for 12 weeks at 40° C., and preferably after 16 weeks at 40° C. However, at elevated temperatures, such as 55° C. or higher, a small amount of brown precipitate may form in the compositions of the present invention. This is due to the thermal decomposition of the organic oxidants employed. Many organic oxidants thermally decompose to generate free radicals at elevated temperatures. When such thermal decomposition occurs, the organic oxidants are less effective at preventing the formation of brown precipitate. Thus, the compositions of the present invention are stable for long periods of time and do not form brown precipitate when stored at temperatures below the thermal decomposition temperature of the oxidant.

Such a limitation is generally not a problem because elevated storage temperatures occur for only short periods.

Dilute solutions prepared according to the present invention do not need additional stabilizer, thus reducing the cost and extra handling associated with known 3-isothiazolone concentrates. One of the further advantages of the present invention is that the 3-isothiazolone dilute solutions do not cause coagulation when added to latexes.

The compositions of the present invention may be used as is or formulated in a variety of ways, such as emulsions and microemulsions. For example, U.S. Pat. No. 5,599,827 (Gironda) discloses microemulsions of a mixture of 5-chloro-2-methyl-3-isothiazolone and 2-methyl-3-isothiazolone, and is herein incorporated by reference to the extent it teaches the preparation of these microemulsions.

The compositions of the present invention can be used to inhibit the growth of microorganisms by introducing a microbicidally effective amount of the compositions onto, into, or at a locus subject to microbial attack. Suitable loci include, but are not limited to: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; industrial disinfectants or sanitizers, such as cold sterilants, hard surface disinfectants; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas. Preferred loci are cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; and metal working fluids.

The amount of 3-isothiazolone compounds suitable to inhibit or control the growth of microorganisms is well known in the art and depends upon the locus to be protected. The amount of 3-isothiazolone microbicide suitable to inhibit the growth of microorganisms is generally between 0.05 and 5,000 ppm, based on the locus to be protected. It is preferred to use between 0.1 and 2,500 ppm. For example, loci such as a cooling tower or pulp and paper processing fluids require 0.1 to 100 ppm of the 3-isothiazolone microbicides to inhibit microorganism growth. In cooling towers or pulp and paper processing fluids, it is preferred to use between 0.1 and 50 ppm. Other loci, such as construction products, oilfield fluids or emulsions, require 0.5 to 5000 ppm of the 3-isothiazolone microbicides to inhibit microorganism growth, while loci such as disinfectants or sanitizers may require up to 5,000 ppm.

It is known in the art that the performance of antimicrobial agents may be enhanced by combination with one or more other antimicrobial agents. Thus, other known microbicidal agents may be combined advantageously with the compositions of the present invention.

The following examples are presented to illustrate further various aspects of the present invention, but are not intended to limit the scope of the invention in any aspect. In the following examples, the 3-isothiazolones used were an approximate 3:1 mixture of 5-chloro-2-methyl-3-isothiazolone and 2-methyl-3-isothiazolone (96.5% pure). The level of copper is reported in ppm as the level of cupric ion. In the following examples, samples were considered stable when at least 80 percent of the 3-isothiazolones remained after 12 weeks of storage at 40° C. and when the samples were free of brown precipitate. All reagents were of good commercial grade and were used without further purification.

EXAMPLE 1

The samples tested were prepared by adding a known amount of DI water to a glass jar equipped with a magnetic stir bar. To this was added a known amount of copper sulfate (as a 1 wt % solution in water), followed by a known amount of an organic oxidant, and lastly a sufficient amount of a 3:1 mixture of 5-chloro-2-methyl-3-isothiazolone and 2-methyl-3-isothiazolone to provide 1.5 wt % of the 3-isothiazolone, based on the weight of the composition. Each sample was stirred until all solids were dissolved and then divided into three portions. One portion was stored at room temperature, one was stored in an oven at 40° C. and the last was stored in an oven at 55° C. The samples were visually examined at various time points to determine the formation of brown precipitate and analyzed by HPLC to determine the amount of 3-chloro-2-methyl-3-isothiazolone ("CMI") remaining. The amounts of the components in each sample are reported in Table 1 and the results are reported in Table 2.

TABLE 1

| Sample | Organic Oxidant (ppm) | 1 Wt % CuSO$_4$ (g) | Oxidant:CUSO$_4$ (mole ratio) | DI Water (g) |
|---|---|---|---|---|
| 1 | peroxyphthalic acid (247 ppm) | 1.18 | 1:1 | 97.26 |
| 2 | peroxyphthalic acid (2470 ppm) | 1.18 | 10:1 | 97.04 |
| 3 | perbenzoic acid (61.1 ppm) | 1.18 | 1:1 | 97.28 |
| 4 | perbenzoic acid (611 ppm) | 1.18 | 10:1 | 97.23 |
| 5 | urea peroxide (47 ppm) | 1.18 | 1:1 | 97.28 |
| 6 | urea peroxide (470 ppm) | 1.18 | 10:1 | 97.24 |
| 7 | 3-chloroperoxy-benzoic acid (86.3 ppm) | 1.18 | 1:1 | 97.28 |
| 8 | 3-chloroperoxy-benzoic acid (869 ppm) | 1.18 | 10:1 | 97.20 |

TABLE 2

| Sample | Weeks of Storage | Temperature (° C.) | Brown Precipitate Formation | CMI Remaining (%) |
|---|---|---|---|---|
| 1 | 0 | 25 | No | |
|   | 4 | 25 | No | |
|   | 4 | 40 | No | |
|   | 4 | 55 | Yes | |
| 2 | 0 | 25 | No | |
|   | 4 | 25 | No | |
|   | 4 | 40 | No | |
|   | 4 | 55 | Yes | |
| 3 | 0 | 25 | No | 100 |
|   | 4 | 25 | No | |
|   | 4 | 40 | No | |

TABLE 2-continued

| Sample | Weeks of Storage | Temperature (° C.) | Brown Precipitate Formation | CMI Remaining (%) |
|---|---|---|---|---|
| | 4 | 55 | Yes | 100 |
| | 8 | 55 | Yes | 97 |
| 4 | 0 | 25 | No | 100 |
| | 4 | 25 | No | |
| | 4 | 40 | No | |
| | 8 | 40 | No | 97 |
| | 4 | 55 | Yes | 100 |
| 5 | 0 | 25 | No | |
| | 4 | 25 | No | |
| | 4 | 40 | No | |
| | 4 | 55 | Yes | |
| 6 | 0 | 25 | No | |
| | 4 | 25 | No | |
| | 4 | 40 | No | |
| | 4 | 55 | Yes | |
| 7 | 0 | 25 | No | |
| | 4 | 25 | No | |
| | 4 | 40 | No | |
| | 4 | 55 | Yes | |
| 8 | 0 | 25 | No | |
| | 4 | 25 | No | |
| | 4 | 40 | Yes | |
| | 4 | 55 | Yes | |

The compositions of the present invention were generally stable and free of brown precipitate at room temperature and after storage at 40° C. The brown precipitate observed in the compositions of the present invention after storage at 55° C. resulted from the decomposition of the organic oxidants at this temperature.

EXAMPLE 2

The procedure of Example 1 was followed except that the organic oxidant was 2,5-dihydroperoxy-2,5-dimethylhexane and the samples were stored at 250 and 40° C. All the samples stored at room temperature were stable and showed no brown precipitate formation. The specific amounts and the results of storage at 40° C. are reported in Table 3. The amount of copper is reported as the amount of cupric ion ("$Cu^{+2}$").

TABLE 3

| Sample | $Cu^{+2}$ (ppm) | Oxidant (ppm) | Weeks of Storage at 40° C. | Brown Precipitate Formation | CMI Remaining (%) |
|---|---|---|---|---|---|
| Control | 0 | 0 | 4 | Yes | 57 |
| Comparative 1 | 0 | 1000 | 4 | Yes | 48 |
| Comparative 2 | 0 | 2000 | 4 | Yes | 44 |
| Comparative 3 | 50 | 0 | 4 | Yes | 80 |
| Comparative 4 | 100 | 0 | 4 | Yes | 85 |
| 9 | 50 | 1000 | 4 | No | 93 |
| | | | 8 | No | 91 |
| | | | 12 | No | 97 |
| | | | 16 | No | 80 |
| 10 | 50 | 2000 | 4 | No | 93 |
| | | | 8 | No | 90 |
| | | | 12 | No | 91 |
| | | | 16 | No | 49 |
| 11 | 100 | 1000 | 4 | No | 96 |
| | | | 8 | No | 90 |
| | | | 12 | No | 100 |
| | | | 16 | No | 89 |
| 12 | 100 | 2000 | 4 | No | 93 |
| | | | 8 | No | 90 |
| | | | 12 | No | |
| | | | 16 | No | 89 |

The above data clearly show that the compositions of the invention are more stable than compositions containing either copper ion alone or an organic oxidant alone and do not form a brown precipitate after 16 weeks of storage.

EXAMPLE 3

The procedure of Example 1 was followed except that the oxidant was tert-butyl hydroperoxide and the samples were stored at various temperatures. The specific amounts and the results of storage are reported in Table 4. The amount of copper is reported as the amount of cupric ion ("$Cu^{+2}$")

TABLE 4

| Sample | $Cu^{+2}$ (ppm) | Oxidant (ppm) | Weeks of Storage (Temp.) | Brown Precipitate Formation | CMI Remaining (%) |
|---|---|---|---|---|---|
| Control | 0 | 0 | 4 (55° C.) | Yes | 80 |
| Comparative 5 | 0 | 42 | 4 (55° C.) | Yes | 0 |
| Comparative 6 | 30 | 0 | 4 (55° C.) | No | 95 |
| | | | 8 (55° C.) | Yes | 79 |
| | | | 24 (40° C.) | Yes | 80 |
| Comparative 7 | 60 | 0 | 4 (55° C.) | Yes | 84 |
| 13 | 30 | 1000 | 16 (40° C.) | No | 91 |
| 14 | 30 | 100 | 16 (40° C.) | No | 89 |
| 15 | 60 | 42 | 4 (55° C.) | No | 87 |
| | | | 12 (25° C.) | No | |
| 16 | 60 | 85 | 4 (55° C.) | No | 85 |
| | | | 12 (25° C.) | No | |
| 17 | 60 | 424 | 4 (55° C.) | No | 84 |
| | | | 12 (25° C.) | No | |

The above data clearly show that the combination of cupric ion and an organic oxidant are useful in stabilizing 3-isothiazolones against decomposition while preventing formation of brown precipitate.

EXAMPLE 4

The procedure of Example 1 was followed except that the oxidant was peracetic acid and the samples were stored at 25° and 55° C. The specific amounts and the results of storage are reported in Table 5. The amount of copper is reported as the amount of cupric ion ("$Cu^{+2}$").

TABLE 5

| Sample | $Cu^{+2}$ (ppm) | Oxidant (ppm) | Weeks of Storage (Temp.) | Brown Precipitate Formation | CMI Remaining (%) |
|---|---|---|---|---|---|
| Comparative 8 | 0 | 36 | 4 (55° C.) | Yes | 0 |
| | | | 12 (25° C.) | Yes | |
| Comparative 9 | 60 | 0 | 4 (55° C.) | Yes | 84 |
| 18 | 60 | 36 | 4 (55° C.) | No | 85 |
| | | | 12 (25° C.) | No | |
| 19 | 60 | 58 | 4 (55° C.) | No | 82 |
| | | | 12 (25° C.) | No | |
| 20 | 60 | 352 | 4 (55° C.) | No | 61 |

The above data show the compositions of the present invention are effective in preventing the formation of brown precipitate upon storage of 3-isothiazolone compositions.

EXAMPLE 5

The procedure of Example 1 was followed except that the oxidant was tert-butyl peroxybenzoate and the samples were stored at 25° C. The specific amounts and the results of storage are reported in Table 6. The amount of copper is reported as the amount of cupric ion ("$Cu^{+2}$").

TABLE 6

| Sample | Cu$^{+2}$ (ppm) | Oxidant (ppm) | Weeks of Storage (Temp.) | Brown Precipitate Formation |
|---|---|---|---|---|
| 21 | 100 | 1000 | 20 (25° C.) | No |

What is claimed is:

1. A stable microbicide composition comprising:
   (a) 0.1 to 5 wt %, based on the weight of the composition, of a water soluble 3-isothiazolone;
   (b) 0.0001 to 0.3 wt %, based on the weight of the composition, of one or more organic oxidants;
   (c) 0.0001 to 0.02 wt %, based on the weight of the composition, of a cupric ion in the form of a copper salt; and
   (d) water;
wherein the composition is free of brown precipitate for at least 12 weeks at 40° C.

2. The composition of claim 1 where the 3-isothiazolone is selected from the group consisting of: 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; and mixtures thereof.

3. The composition of claim 1 wherein the organic oxidant is selected from the group consisting of: tert-butyl hydroperoxide, 2,5-dihydroperoxy-2,5-di-methylhexane, di-tert-butyl hydroperoxide, 2-butanone peroxide, tert-butyl peroxybenzoate, tert-butyl peroxyacetate, tert-butyl peracetate, tert-butyl peroctoate, benzoylperoxide, succinic acid peroxide, urea peroxide, peracetic acid and mixtures thereof.

4. The composition of claim 1 wherein the copper salt is selected from the group consisting of: copper sulfate, copper acetate, copper chloride, copper bromide, copper chlorate, copper perchlorate, copper nitrite and copper nitrate.

5. The composition of claim 1 further comprising a solubilizer for the organic oxidant.

6. A method of stabilizing a microbicide composition comprising the step of adding 0.0001 to 0.3 wt %, based on the weight of the composition, of an organic oxidant; and 0.0001 to 0.02 wt %, based on the weight of the composition, of a cupric ion in the form of a copper salt to a 3-isothiazolone composition comprising 0.1 to 5 wt %, based on the weight of the composition, of a water soluble 3-isothiazolone compound; and water.

7. The method of claim 6 wherein the copper salt is selected from the group consisting of: copper sulfate, copper acetate, copper chloride, copper bromide, copper chlorate, copper perchlorate, copper nitrite and copper nitrate.

8. The method of claim 6 wherein the organic oxidant is selected from the group consisting of: tert-butyl hydroperoxide, 2,5-dihydroperoxy-2,5-dimethylhexane, di-tert-butyl hydroperoxide, 2-butanone peroxide, tert-butyl peroxybenzoate, tert-butyl peroxyacetate, tert-butyl peracetate, tert-butyl peroctoate, benzlperoxide, succinic acid peroxide, urea peroxide, peracetic acid and mixtures thereof.

9. A method of controlling or inhibiting the growth of microorganisms in a locus comprising introducing to the locus the composition of claim 1.

10. The method of claim 9 wherein the locus is selected from the group consisting of: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; and metal working fluids.

* * * * *